United States Patent [19]
Rahbari

[11] Patent Number: 5,620,472
[45] Date of Patent: Apr. 15, 1997

[54] APPARATUS AND METHOD FOR DYNAMICALLY INTERPRETING AND DISPLAYING A REAL-TIME TELEMETRY LINK

[75] Inventor: Azita M. Rahbari, Newbury Park, Calif.

[73] Assignee: Pacesetter, Inc., Sylmar, Calif.

[21] Appl. No.: 372,489

[22] Filed: Jan. 12, 1995

[51] Int. Cl.[6] .................................................. A61N 1/37
[52] U.S. Cl. ................................ 607/27; 128/903
[58] Field of Search .................. 128/903; 607/27, 607/30, 31, 32, 59, 60

[56] References Cited

U.S. PATENT DOCUMENTS

| | | | |
|---|---|---|---|
| 4,305,397 | 12/1981 | Weisbrod et al. | 607/30 |
| 4,432,360 | 2/1984 | Mumford et al. | 607/30 |
| 4,561,443 | 12/1985 | Hogrefe et al. | 128/903 |
| 5,107,833 | 4/1992 | Barsness | 128/903 |
| 5,354,319 | 10/1994 | Wyborny | 607/32 |
| 5,400,794 | 3/1995 | Gorman | 128/903 |

*Primary Examiner*—William E. Kamm

[57] ABSTRACT

A monitoring and/or programming device communicates with a cardiac stimulation device, such as a pacemaker, which is operatively implanted within a patient. Communication between the programmer and cardiac device occurs over a radio frequency (RF) telemetry link. During a monitoring and/or programming procedure, data is transmitted over the RF telemetry link between the programming device and the cardiac device. Parameters indicating the quality of the RF telemetry link are continuously measured, evaluated and formatted for display to an operator of the programming device.

62 Claims, 9 Drawing Sheets

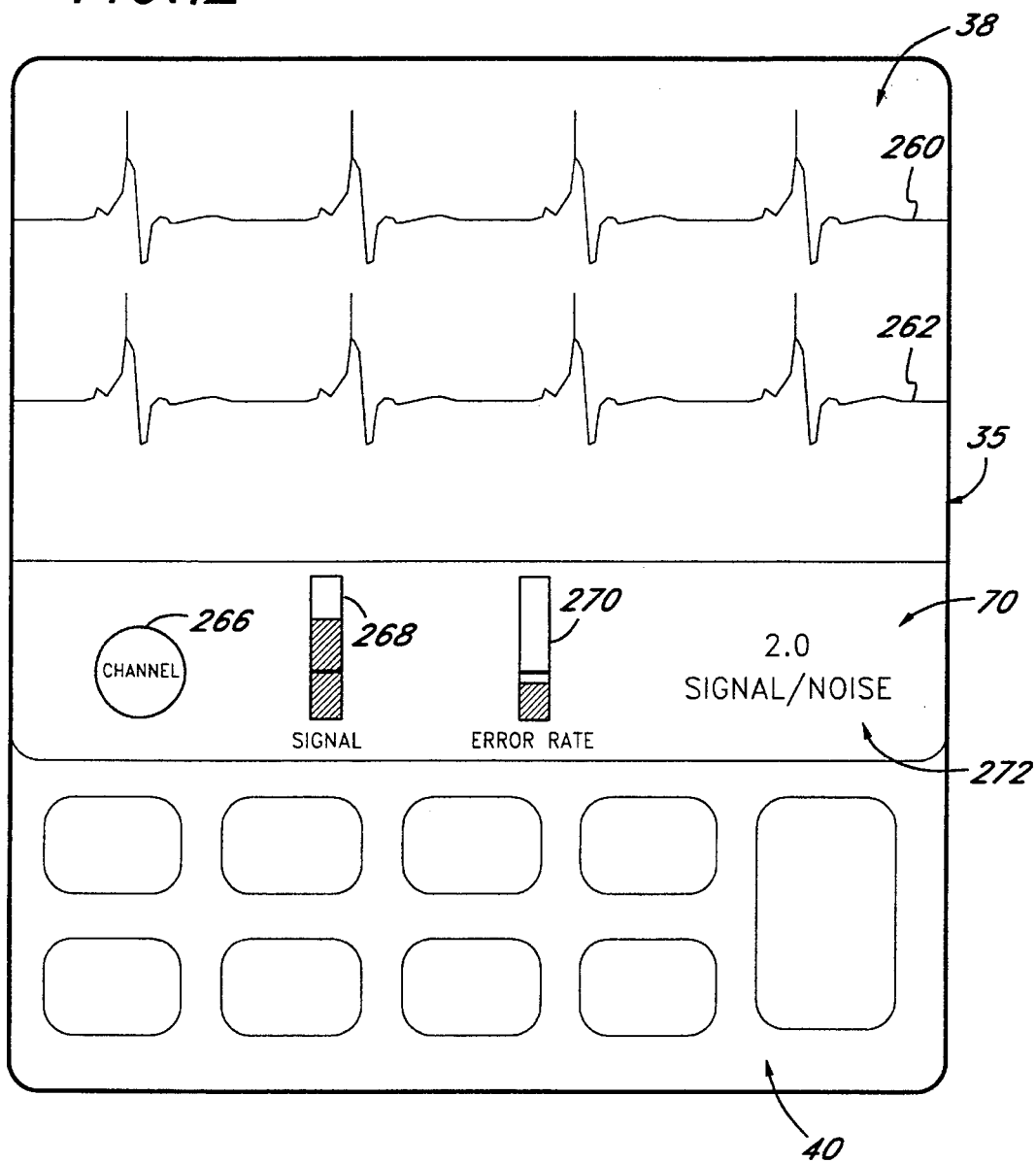

APPARATUS AND METHOD FOR DYNAMICALLY INTERPRETING AND DISPLAYING A REAL-TIME TELEMETRY LINK

FIELD OF THE INVENTION

This invention relates generally to cardiac stimulation devices, e.g., pacemakers, and apparatus for monitoring and programming such stimulation devices over a radio frequency (RF) telemetry link. More particularly, this invention relates to apparatus and methods for monitoring the status and quality of the RF telemetry link used for communicating between a cardiac stimulation device and an associated programming device.

BACKGROUND OF THE INVENTION

Cardiac pacemakers, and other cardiac stimulation devices, such as defibrillators, are now routinely used by physicians around the world. These devices are surgically implanted within a patient and have electrical leads that conduct signals to the patient's heart. Advances in the electrical and electronic technologies have been applied to pacemaker devices to improve the performance, reliability, and programmability of such pacemakers. Many of these advances are exploited by using a communication link established between an implanted pacemaker and a device called a "programmer". For example, pacemakers in use today have the ability to communicate with a programmer via an RF link. The programmer can receive data from the pacemaker as well as transmit both data and programming instructions to the pacemaker. A communication channel is established between a pacemaker and a programmer by placing a telemetry head, which is connected to the programmer, over the implant site (e.g., chest or abdomen) of a patient. The telemetry head functions as an antenna for transmitting and receiving RF signals.

Once an operational telemetry link is established between a pacemaker device and a programmer unit, data transfer between the two devices can occur. During this data-transfer period, information representing the patient's past heart activity is typically downloaded from the pacemaker to the programmer. Additionally, the pacemaker will typically transmit real-time data representing the patient's present cardiac activity. In some cases, the communication link is used to program and reprogram the pacemaker.

During the real-time data transmission, the telemetry link between the pacemaker and the programmer can be disrupted. Disruption of the telemetry link can result from relative movement between the patient (i.e., pacemaker), and the telemetry head. Disruption of the communication channel can also result from excessive noise picked up by the telemetry head, or when the telemetry head and the pacemaker become separated by too great a distance. If any of these conditions occur, the communication link may be broken and all data transmission will correspondingly cease. Typically, the attending medical personnel first realize a problem exists with the communication link when he or she attempts to communicate with the device. Once broken, it is necessary for the physician to reestablish the communication link to continue the monitoring and/or programming procedure. This process is time-consuming and delays the intended operation.

Aside from being time consuming, problems with obtaining and maintaining an adequate RF communication link can lead to catastrophic results. For example, an attending physician who experiences difficulty in establishing or maintaining a communication link with an implanted pacemaker may take improper action if the physician does not know the precise reason for the difficulty. Specifically, without information as to the status and quality of the communication link, the physician may conclude that the pacemaker is defective. In such a situation, the physician could erroneously recommend replacement of the pacemaker when, in fact, the problem could have been corrected without invasive surgery by establishing a proper communication link.

Advances in pacemaker technology have resulted in various improvements in the way data is transmitted between the pacemaker and the programmer. Other improvements relate to methods of processing the data. For example, in U.S. Pat. No. 4,596,255 issued to Snell et al., there is disclosed an apparatus connected to an implanted pacemaker which interprets and displays a patient's cardiac events. The apparatus disclosed in Snell simultaneously receives information from the pacemaker and information from ECG electrodes placed on the patient. The information from the pacemaker is synchronized with the information from the ECG and subsequently displayed in real-time on a video screen. This allows an attending physician to quickly evaluate the functioning of both the pacemaker and the patient's heart.

Disclosed in U.S. Pat. No. 4,791,936, also issued to Snell et al., is a separate apparatus for interpreting and displaying a patient's cardiac activity in conjunction with the signals generated by a cardiac pacemaker. The apparatus disclosed utilizes multiple interpreters to process information received from a telemetry head, which in turn receives the information from the pacemaker via an RF communication link. According to the '936 patent, the information received represents different cardiac events, such as atrial or ventricular contractions. This information, along with ECG information received from a separate interpreter, is synchronized. The resulting synchronized information is then processed before being displayed on a video screen in real-time.

Other patents which disclose apparatus and methods for communicating with, monitoring, and/or programming the actions of a pacemaker include U.S. Pat. No. 4,809,697 issued to Causey, III et al., and U.S. Pat. No. 5,309,919 issued to Snell et al.

All of the above-described patented devices use noninvasive telemetry to configure the specific operation of the pacemaker in accordance with the needs of an individual patient. Noninvasive telemetry is accomplished through the use of an RF communication channel. While various ways have been developed to improve the type and amount of data received through this communication channel and the format of displaying the data, little attention has been directed to the monitoring of the quality of the communication channel.

When monitoring and/or programming cardiac pacemakers, the quality of communication is important because many problems associated with telemetry occur if the telemetry link, i.e., the communication channel, is never properly established. In some problematic cases, the telemetry link may at first be properly established but for any of a number of possible reasons, the link is subsequently broken. Thus, there is a need in the art for a telemetry system which can monitor the status and quality of the communication channel to correct deficiencies in channel quality during the procedure of communicating with, and programming a cardiac stimulation device.

SUMMARY OF THE INVENTION

The present invention comprises an apparatus for continuously monitoring the status and quality of a radio frequency (RF) communication link which is used for transmission of data signals between a cardiac stimulation device and an associated programming device. The programming device communicates with the cardiac device, through the use of a telemetry head, during monitoring and programming sessions performed by a physician or other attending medical personnel. The apparatus also processes the channel status/quality information and displays this information for viewing by the attending medical personnel.

The monitoring apparatus operates in association with a programming device to perform periodic measurements of the channel quality. These measurements are performed during the procedure for monitoring and programming the pacemaker. A number of different channel quality parameters may be measured for display and feedback to the attending medical personnel.

One of the parameters indicating channel quality is the strength of the RF signal transmitted by the pacemaker. A stronger pacemaker signal improves the chances of accurate data transmission. Conversely, the strength of any surrounding or interfering noise may adversely affect accurate data transmission. In the preferred embodiment, both of these parameters are measured to determine their relative strength.

Another parameter that may be measured to provide an indicia of signal quality is the data error rate. Because the data between the pacemaker and the programmer is transmitted in a digital format, the number of incorrect bits transmitted through the RF link can be measured and processed to produce a relative error rate. The error rate can be an important factor in determining when signal amplitude and/or noise amplitude, or lack thereof, is affecting the transmission of data.

The preferred embodiment of the present invention combines certain channel quality parameters which are displayed to attending medical personnel. For example, the parameters for signal amplitude and noise amplitude can be used to generate a signal-to-noise ratio for display on the programming device. Other combinations of the channel quality data can be specially configured to convey particular information depending on the particular patient, the particular cardiac stimulation device, or on other circumstances.

The status of the communication channel as either open or closed may be continuously monitored by comparing the magnitude of the channel quality parameters with predetermined threshold values. Alternatively, an operative channel status may be confirmed by verifying the exchange of data between the pacemaker and the programmer. Information reflecting the channel status is processed and displayed separately to provide feedback to the user. The programmer can reopen and establish a telemetry link with the cardiac stimulation device when the channel is reported to be closed. This automatic reopening of the communication channel will be under user control.

In the preferred embodiment, channel status and channel quality are conveyed as feedback information to an attending physician in the form of a graphical display which appears on a video screen of the programming device. Also, it is possible to display the feedback information on the telemetry head using a liquid crystal (LCD), or other form of display. Such feedback information regarding the status and quality of the communication channel is important for facilitating interaction with an implanted pacemaker.

The present invention thus aids medical personnel in both establishing a communication telemetry link, and in maintaining that link during monitoring and programming of an associated pacemaker device.

BRIEF DESCRIPTION OF THE DRAWINGS

The above and other aspects, features and advantages of the present invention will be more apparent from the following more particular description thereof presented in conjunction with the following drawings wherein:

FIG. 11 is a graphical representation of indicia depicting the signal-to-noise ratio in accordance with the present invention.

FIG. 12 is an illustration of a display screen upon which multiple graphical representations of channel status and quality are displayed.

DETAILED DESCRIPTION OF THE PREFERRED EMBODIMENT

The present invention is an apparatus for monitoring the status and quality of an RF communication channel, over which data is transmitted between a cardiac pacemaker and an associated programming device. In the preferred embodiment, a number of parameters indicating the channel status and quality are measured, interpreted, and finally displayed on a video screen of the programming device. Display of this information provides feedback to appropriate medical personnel during procedures for monitoring and programming a cardiac pacing device.

Figure 1:
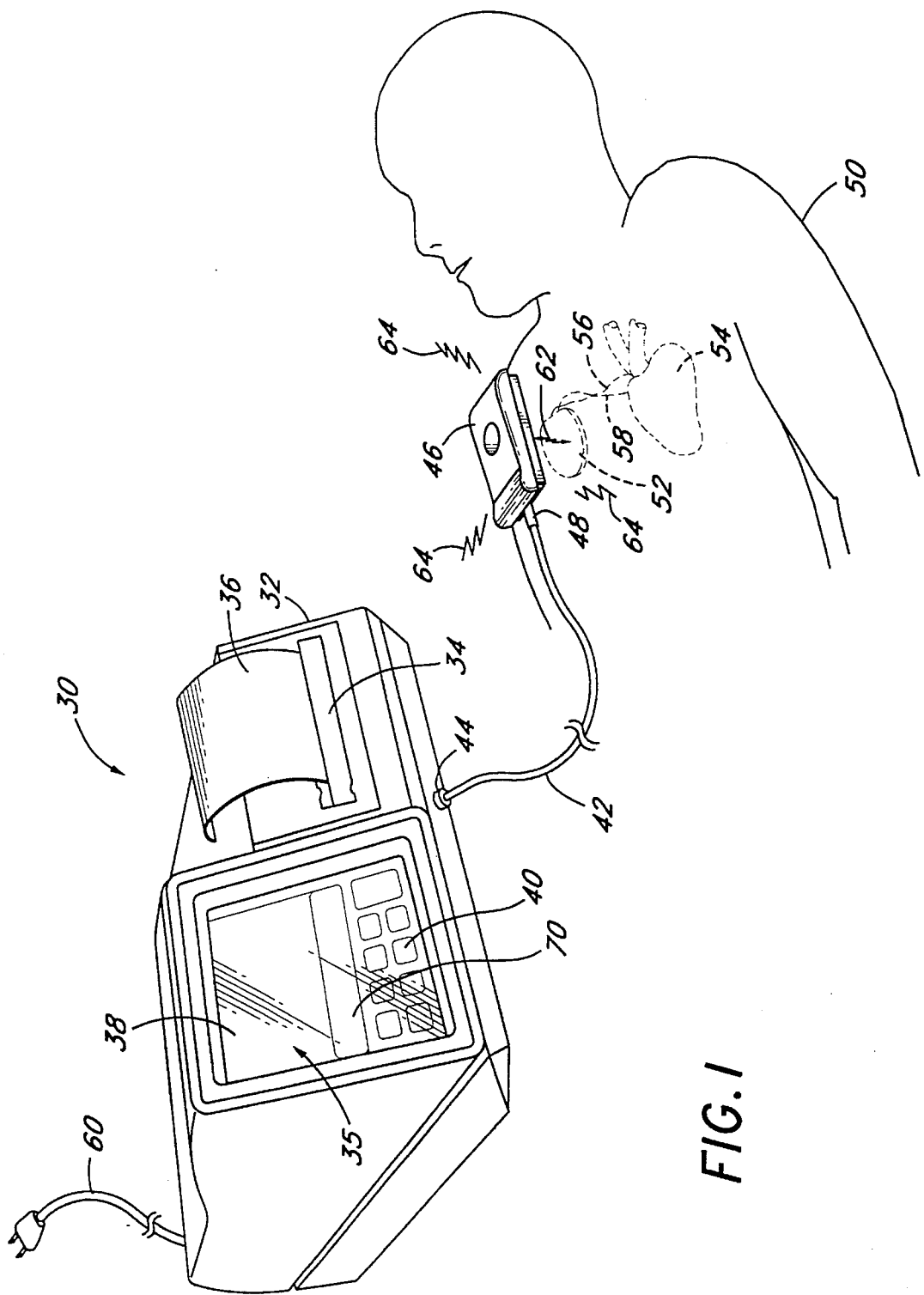
FIG. 1 is a perspective view illustrating a programmer with a telemetry head positioned for monitoring and programming a cardiac stimulation device implanted within a patient.

In FIG. 1, there is shown a perspective view of the present invention in operative association with a patient 50. An electronic monitoring device, referred to as a "programmer", is shown and is generally designated 30. The programmer 30 comprises an outer casing 32, which encloses a printing mechanism 34, for printing cardiac information onto a paper copy 36. A communication cable 42 is attached at one end to the casing 32 by a connector 44. A telemetry head 46 is connected at the opposite end of the cable 42 by another connector 48.

The programmer 30 also includes a video display screen 35, which comprises three separate screen segments. These segments include a cardiac waveform/parameter segment 38, a channel information segment 70, and a keypad segment 40. The video display screen 35 is touch-sensitive allowing user commands to be formatted for display on the video display screen 35, and then selected when a user touches the appropriate command, i.e., a given area of the video display screen 35. It can be appreciated that although the display 35 is shown with segregated screen segments 38 and 70, the channel information intended for display on the segment 70, can also be displayed on the segment 38. In FIG. 1, user commands are formatted for display on the keypad segment 40. Additional user commands may be displayed on the waveform/parameter segment 38 and the channel information segment 70. Alternatively, an assortment of permanent, or dedicated, buttons may be used instead of the keypad segment 40.

During a typical programming and/or monitoring procedure for a pacemaker 52, the telemetry head 46 is placed upon the chest of the patient 50 and positioned above the pacemaker 52 which is implanted within the patient 50. The implanted pacemaker 52 is operatively connected to the patient's heart 54 via leads 56 and 58.

The programmer 30 is powered through use of a power cord 60 connected to a typical electrical AC outlet socket (not shown). The programmer 30 communicates with the implanted pacemaker 52 by transmitting data over a radio frequency (RF) communication channel 62 which exists between the telemetry head 46 and the pacemaker 52 as shown in FIG. 1.

An operator of the programmer 30, such as an attending physician or other medical personnel (not shown), will begin a typical pacemaker programming and/or monitoring session by first energizing the programming unit 30 and establishing the communication channel 62 between the telemetry head 46 and the pacemaker 52. To establish the communication channel 62, the operator first places the telemetry head 46 upon the chest of the patient 50. Desirably, the telemetry head 46 is placed at a point closest to the implanted pacemaker 52. This allows for the shortest transmission path of data over the RF communication channel 62. Once the telemetry head 46 is placed near the pacemaker 52, the attending physician will begin an initialization sequence to establish, i.e., "open", the communication channel 62. Opening the communication channel 62 is performed by first transmitting coded data from the telemetry head 46 to the pacemaker 52 for verification. The pacemaker 52 receives the data, verifies the data, and transmits an RF signal back to the telemetry head 46. Numerous communication methods can be used to transmit data over the communication channel 62. A more detailed explanation of various methods for communicating with an implanted pacemaker can be found in U.S. Pat. No. 4,791,936 issued to Snell et al., the full text of which is incorporated herein by reference as though fully set forth herein.

After establishing a communication link over the communication channel 62, the attending physician can then choose one of several functions displayed on the keypad 40 to begin a programming and/or monitoring procedure. Information relating to these functions may then be displayed on the video screen 35. During such a procedure, data will be transmitted from the pacemaker 52 to the telemetry head 46, and vice-versa, over the RF communication channel 62.

In a typical programming and/or monitoring procedure, stray RF signals 64 are often present. These stray signals 64 can interfere with accurate data transmission over the RF communication channel 62 by affecting the quality of the communication channel 62. In an extreme case, the stray signals 64 can prevent the communication channel 62 from being initially opened, or if opened, the stray signals 64 may cause interruption of the communication channel 62.

The programmer 30 evaluates the state of the communication channel 62 and relays this information to an operator. Specifically, hardware inside the casing 32 measures certain parameters relating to the communication channel 62, processes these parameters, and displays them on the segment 70 of the video screen 35. By viewing the channel information segment 70, the operator can observe any problems with the channel quality and then make adjustments to prevent the interruption of the communication channel 62. Correction of such problems may require nothing more than slight movement of the telemetry head 46, the patient 50, or adjustment/movement of other equipment (not shown) that may be in the patient's room and which may be emitting the stray signals 64.

Figure 2:
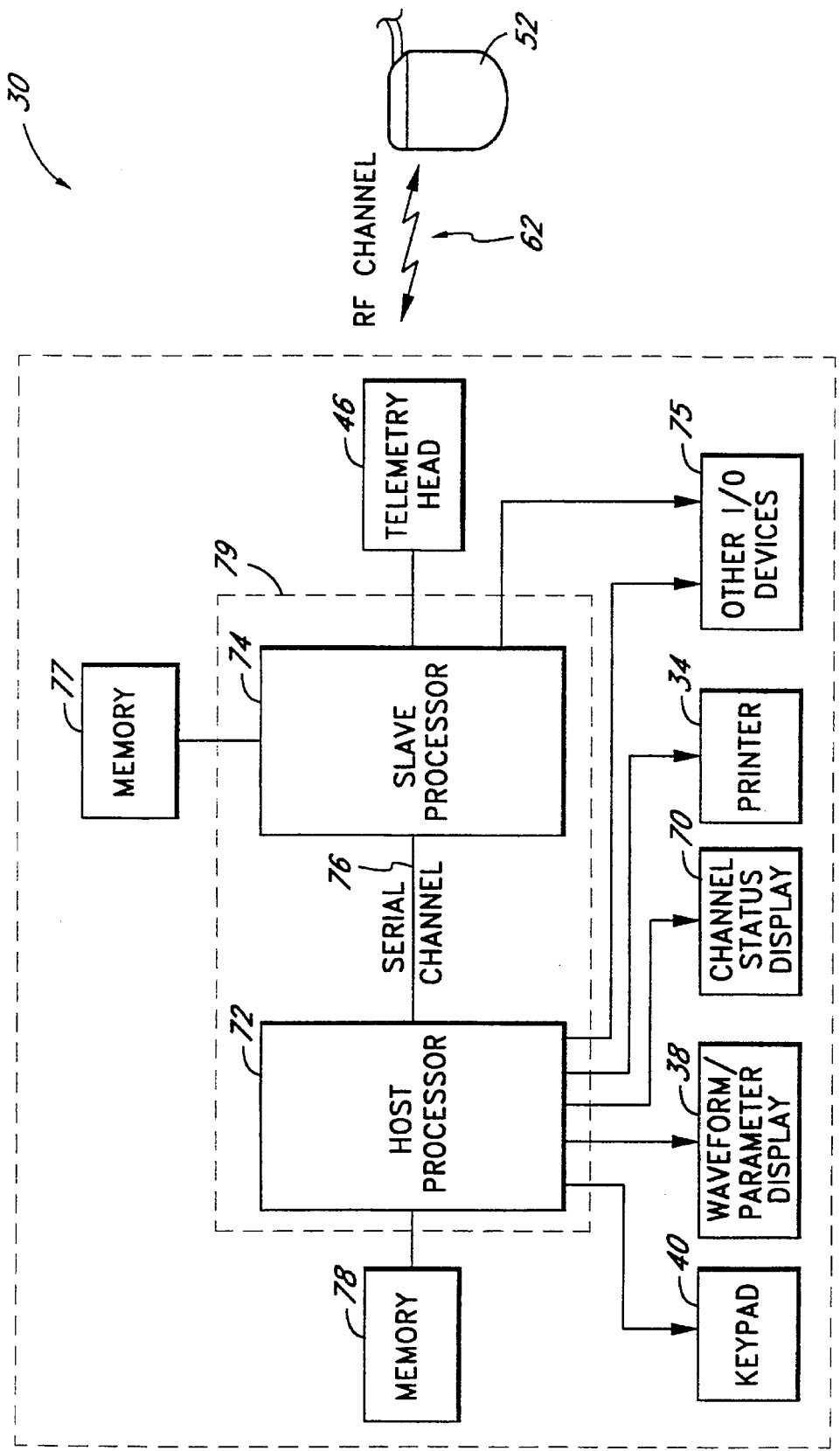
FIG. 2 is a block diagram of the hardware associated with the present invention.

In FIG. 2, a block diagram is presented depicting the components of the programmer 30, and depicting the pacemaker 52. The programmer 30 comprises a host main processor 72 connected to a slave processor 74 via a serial channel 76. The host processor 72 interacts and is connected to a memory unit 78, the printer 34, the waveform/parameter display segment 38, the channel information display segment 70, and the keypad 40. The displays 38, 70 comprise video displays, such as LCDs in which pixels are physically altered to depict various graphics or other indicia. The keypad 40 may comprise such video displays, or may in the alternative comprise permanent buttons. The host processor and slave processors 72, 74 are also connected to other selected input/output devices 75 which may include a keyboard, data storage devices, patient ECG leads, etc. As shown in FIG. 2, the slave processor 74 interacts and is connected to a memory unit 77 and the telemetry head 46. The telemetry head 46 communicates with the pacemaker 52 over the RF channel 62.

Data received by the telemetry head 46 is processed by the processors 72, 74 and is presented on the appropriate display, such as the waveform/parameter display segment 38, and/or printed by the printer 34. The memory module 78 interacts with the host processor 72 to store and provide access to data, as required by the processor 72. Likewise, the memory module 77 interacts with the slave processor 74 to store and provide access to data, as required by the processor 74. The portion of the data relating to the status and quality of the communication channel 62 is processed by the slave and host processors 72, 74 for display on the channel information display segment 70.

Figure 3:
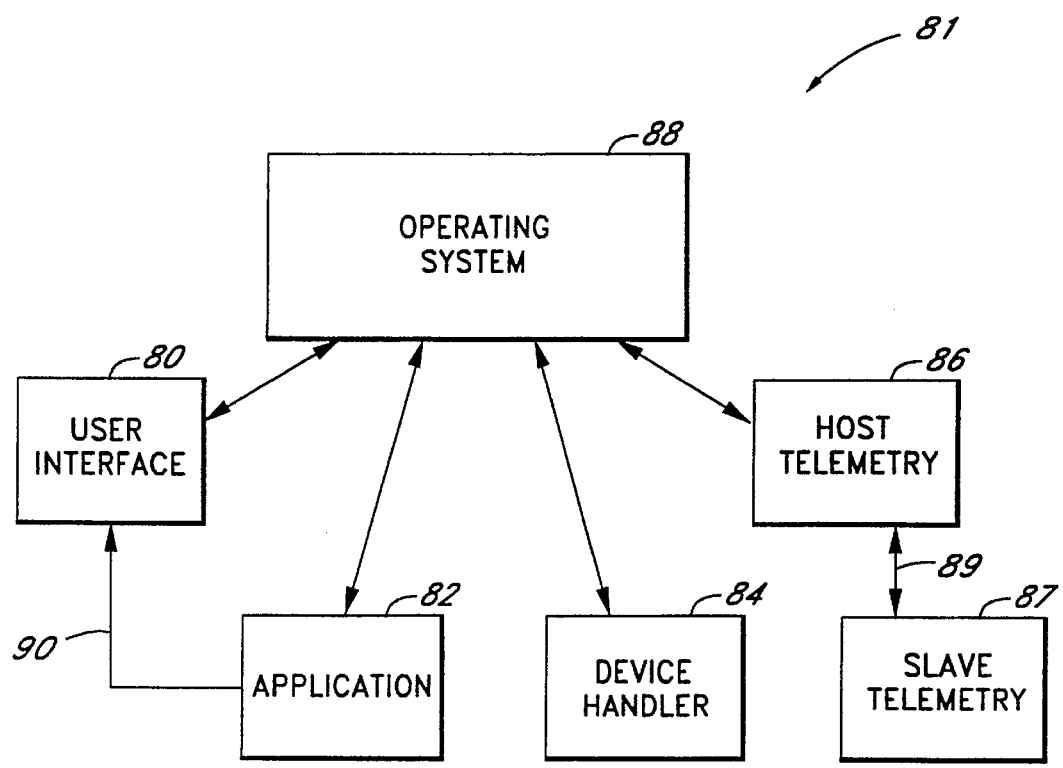
FIG. 3 is a block diagram of the software subsystems of the present invention.

FIG. 3 is a block diagram representing the software architecture 81 utilized in the processing arrangement 79 (shown in FIG. 2). According to the preferred embodiment, the software architecture is comprised of five subsystems. These subsystems include a user interface subsystem 80, an application subsystem 82, a device handler subsystem 84, a host telemetry subsystem 86, and a slave telemetry subsystem 87. The first four subsystems 80, 82, 84, and 86 are all interconnected to an operating system 88, which is used to control the execution of the four subsystems, and communication between the subsystems. The slave telemetry subsystem 87 interfaces with the host telemetry subsystem 86 over a serial interface 89.

The user interface subsystem 80 resides in the host processor 72 (shown in FIG. 2) and controls the user input and output. The application subsystem 82 also resides in the host processor 72 and is the top-level manager of the software architecture 81. The subsystem 82 translates user requests for the device handler subsystem 84. The application subsystem 82 also formats screen and printer outputs for the user interface subsystem 80, as represented by a communication line 90. The device handler subsystem 84 is invoked by the application subsystem 82 and is responsible for generating the correct sequence of commands transmitted to a pacemaker device (not shown) by the slave telemetry subsystem 87. The device handler subsystem 84 also resides in the host processor 72 (shown in FIG. 2). The host telemetry subsystem 86 receives requests generated by the device handler, and in turn, generates corresponding requests for the slave. The slave telemetry subsystem 87 then generates the necessary communication protocol with an associated pacemaker (not shown). The host telemetry subsystem 86 resides in the host processor 72 (shown in FIG. 2), and the slave telemetry subsystem 87 resides in the slave processor 74 (shown in FIG. 2). A more detailed functional description of the hardware and software for a typical programmer can be found in U.S. Pat. No. 4,809,697 issued to Causey, III et al. An exemplary device that employs the five subsystems described in conjunction with FIG. 3 herein is the APS II programmer Model No. 3003, available from Pacesetter of Sylmar, Calif.

In order to monitor the status and quality of the communication channel 62 during a pacemaker programming procedure, the processing arrangement 79 (shown in FIG. 2) performs various operations under the control of the software architecture 81 (shown in FIG. 3). This dynamic monitoring of the communication channel 62 is performed by utilizing both the host main processor 72 and the slave processor 74 of the processing arrangement 79.

Figure 4:
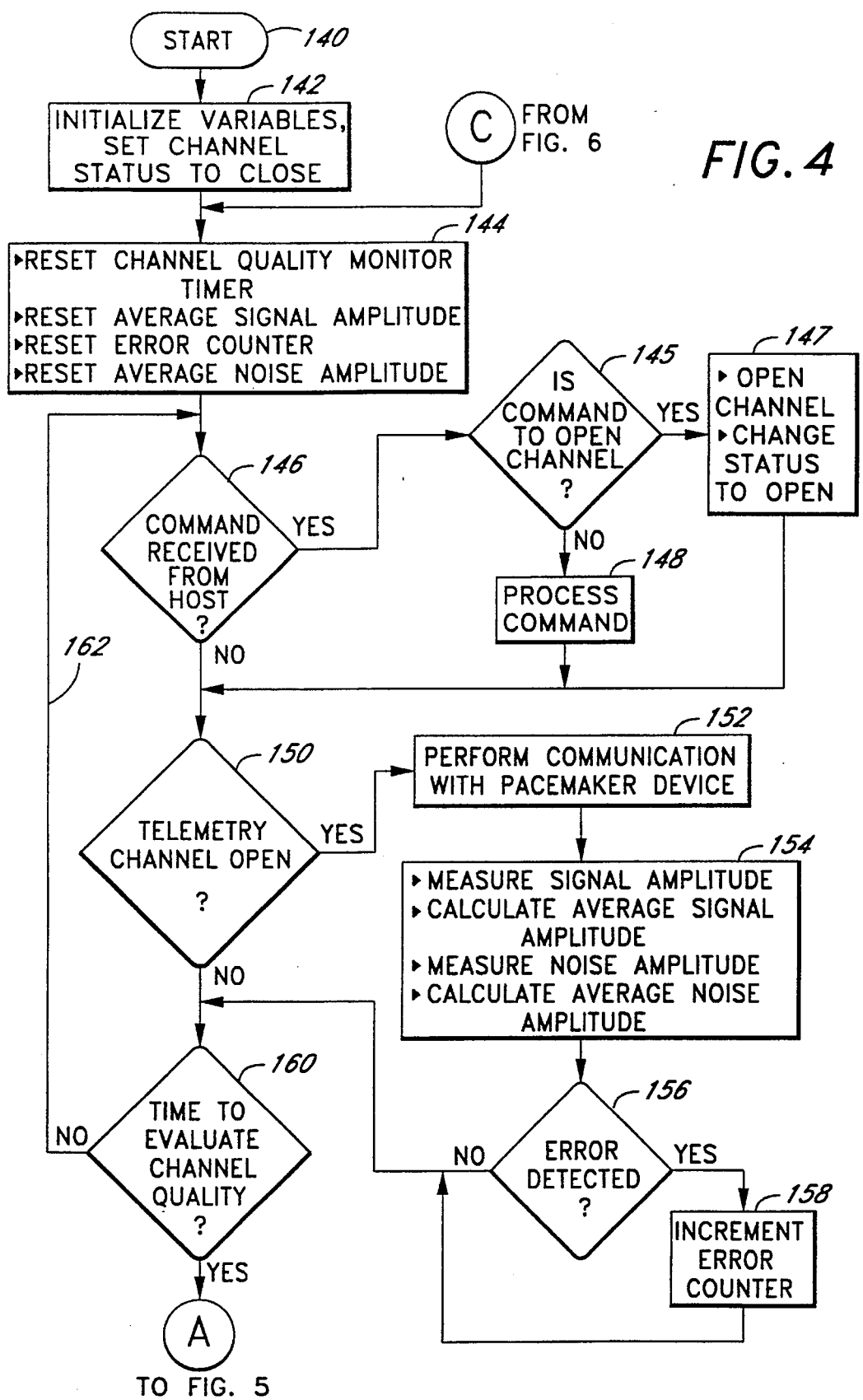
FIG. 4-6 are flowcharts showing the operations performed by the slave software in monitoring the channel status and quality.
Figure 5:
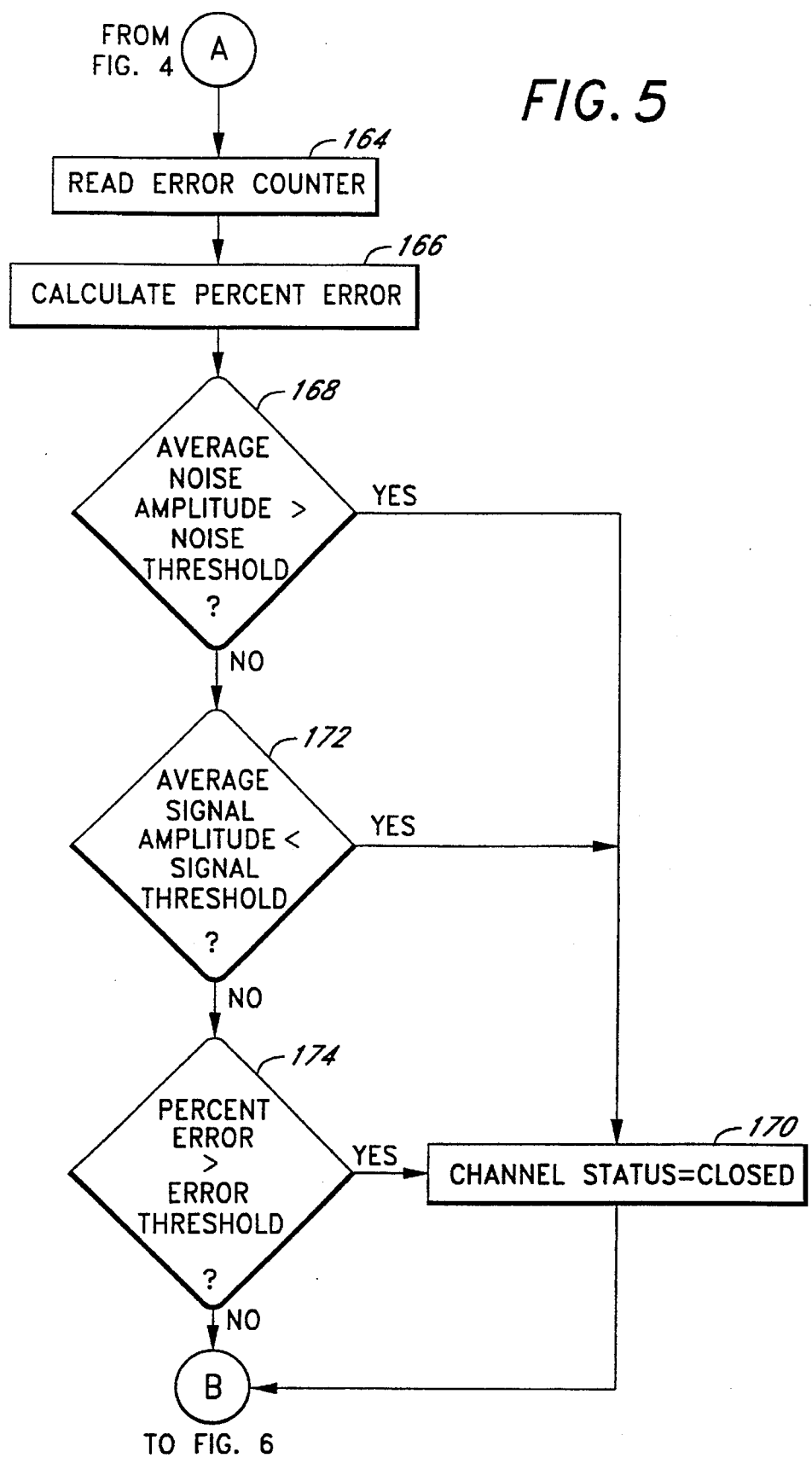
Figure 6:
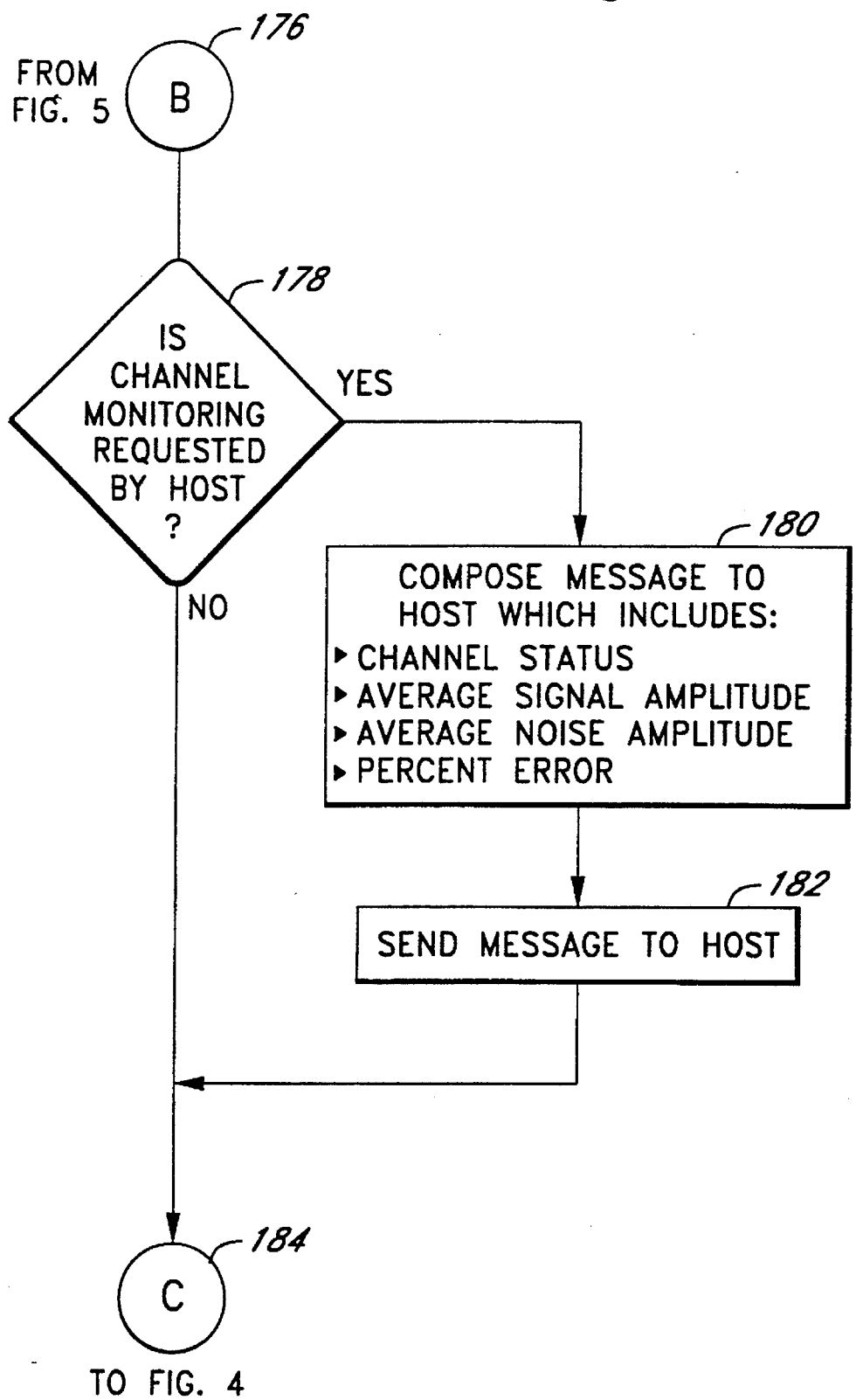
Figure 7:
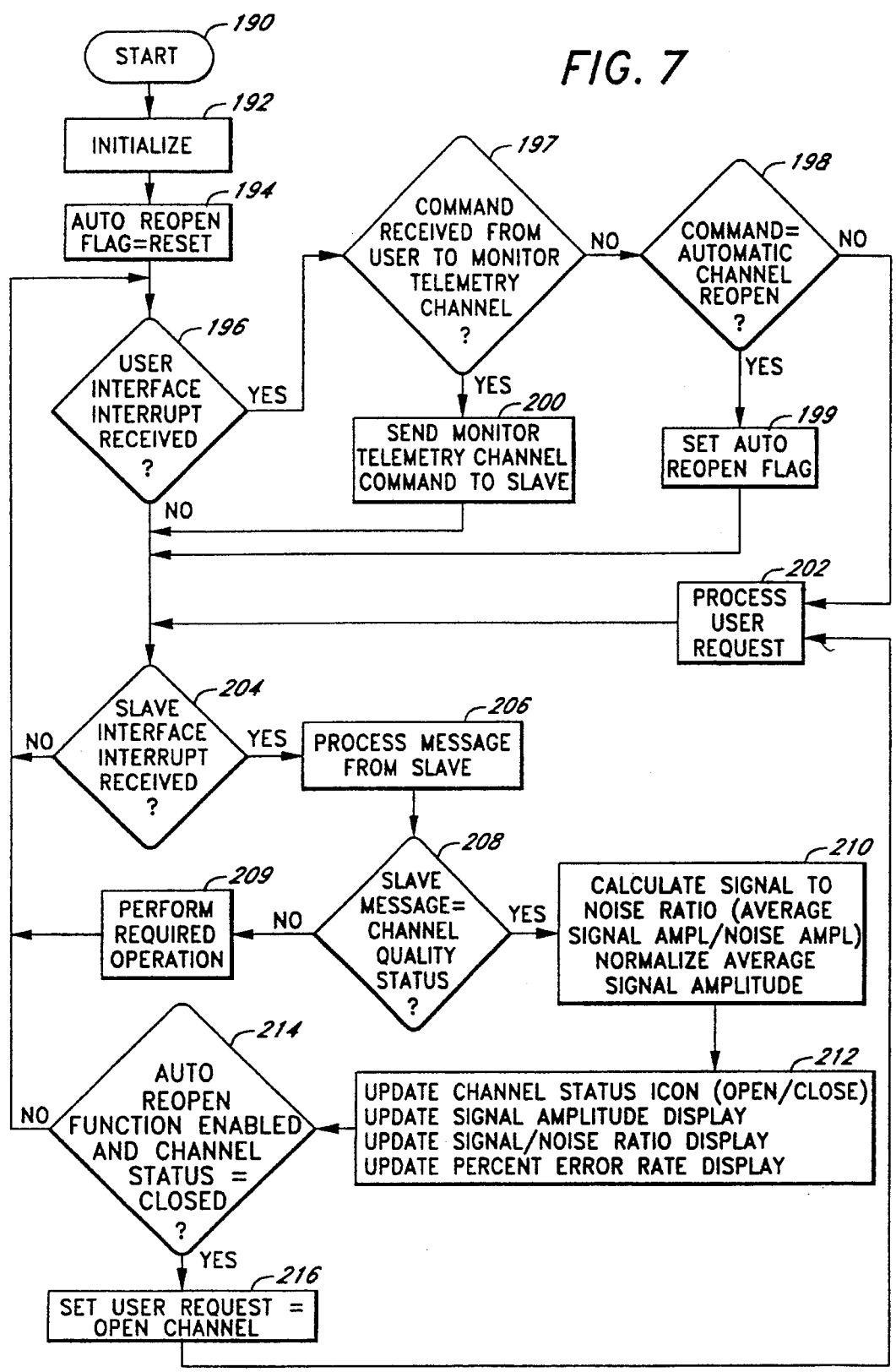
FIG. 7 is a flowchart depicting the operations performed by the host software in monitoring the channel status and quality.

FIGS. 4–7 are flowcharts depicting the operation of the processing arrangement 79 (shown in FIG. 2), as dictated by the software architecture 81 (shown in FIG. 3), for dynamically monitoring and representing the quality and status of the communication channel 62 (shown in FIG. 1). More specifically, FIG. 4–6 are flowcharts depicting the sequences performed within the slave processor 74, while FIG. 7 is a flowchart depicting the sequences performed within the host processor 72. The process steps performed by the processing arrangement 79 are separated into those performed within the host processor 72 and those performed within the slave processor 74 because these routines run separately yet interact with each other.

In FIG. 4, the process for monitoring the status and quality of the RF communication channel 62 begins from a start state 140 and enters an initialize state 142. Within the initialize state 142, the status of the communication channel 62 is set to "closed." Also within the state 141, variables and registers used in the monitoring process are set to their default values. After initialization, the process flow enters an activity state 144 in which the specific channel quality parameters are reset. One of these parameters is the channel-quality-monitor timer, which determines the interval at which the status and quality of the communication channel is updated. Other parameters which are reset in the state 144 include the channel-quality indicators of average signal amplitude, average noise amplitude, and the error counter. Once the channel quality parameters are reset, process flow exits the state 144 and enters a decision state 146. In the decision state 146, the slave processor 74 (not shown) determines whether a command has been received from the host processor which requires attention. If no such command is received within the decision state 146, control directly enters a decision state 150 from the state 146. If such a command is received within the decision state 146, control is transferred to another decision state 145 to determine if the command received was a request to open the communication channel 62 (shown in FIG. 1) with the pacemaker. If the command was not a request to open the communication channel 62, control passes to an activity state 148 where the command is processed by the slave. After processing in the state 148, control then enters the decision state 150. If the command evaluated in the state 145 was a request to open the communication channel 62, control exits the decision state 145 and passes to an activity state 147 in which the slave opens the communication channel 62. The slave typically opens the communication channel 62, i.e., an RF channel is established, with the pacemaker device by sending a sequence of pulses to the pacemaker based on an established communication protocol. Once the communication channel is opened, an appropriate "flag" can be set to indicate the channel status (open or closed), and control then returns to the decision state 150.

In the decision state 150, the slave processor determines whether or not the telemetry channel, i.e., the communication channel, is open. The process flow directly enters a decision state 160 from the decision state 150 when it is determined that the telemetry channel is not open. Assuming the process flow has already proceeded through state 147, the channel status flag will be set to "open." If the channel is open, process flow proceeds from the decision state 150 into an activity state 152 during which communication is performed with the pacemaker. After communication has occurred, i.e., data has been transmitted either to or from the pacemaker device, process flow enters another activity state 154. Within this state 154, the slave processor will measure the values of at least one of several parameters which indicate the quality of the communication channel. These parameters include the amplitude of the signal received from the pacemaker device, and the amplitude of any surrounding noise which is received by the telemetry head (shown in FIG. 1).

Communication between the telemetry head and the pacemaker is performed by dividing the communication period into individual data transmission periods, or frames, which, in the preferred embodiment, are approximately eight milliseconds long. Within these eight-millisecond frames, there exists a portion of time during which data is transmitted either to or from the pacemaker device. There are also portions of time during which no data is transferred between the pacemaker and the telemetry head.

Within the state 154 and during a given data transmission period, the amplitude of the data signal is measured, and the amplitude of any stray noise is measured. These measurements yield a signal level and a noise level, respectively. In the preferred embodiment, information regarding data signal and noise amplitudes is not transmitted to the host processor for display after each eight-millisecond data frame. Typically, several data frames will elapse before the information is transferred to the host. For this reason, the state 154 also calculates an average value for the signal and noise amplitudes for the preceding data frames. Once these measurements and calculations are made, the process flow exits the state 154 and enters a decision state 156.

Within the state 156, the slave processor 74 (not shown) will determine whether an error has occurred during the transmission of data. If an error has occurred, control enters an activity state 158 in which the error counter is incremented. If no error is detected in the state 156, or after the error counter has been incremented in the state 158, process flow enters the decision state 160.

Within the decision state 160, a determination is made whether the current state and quality of the communication channel should be evaluated. As mentioned above, the signal and noise amplitudes, while measured in each data frame, are not processed and sent to the host processor 72 (shown in FIG. 2) in each of these frames. Instead, the channel quality parameters are averaged over a predetermined interval before being sent to the host processor 72. Therefore, the decision state 160 is required to regulate the interval at which a channel-status message is sent to the host. If it is determined in the state 160 that the channel quality should not be monitored, process flow will revert back through path 162 and into the decision state 146. From the decision state 146, process steps 148–158 may again be repeated for a separate communication frame. Upon reentering the state 154, the signal and noise amplitudes will be remeasured, and then averaged with the measurements made during the preceding communication frame. If there are no preceding measurements because process flow has just exited the state 144, then no averaging occurs.

If it is determined within the decision state 160 that the elapsed time requires monitoring of the communication channel quality, control exits the decision state 160 and enters a state 164 shown in FIG. 5. Typically, the time interval for evaluating the channel quality within the state 160 is set to equal approximately 100 milliseconds. This interval may be reduced or increased depending on the particular system requirements without affecting the dynamic and continuous aspect of channel monitoring disclosed herein.

FIG. 5 is a continuation of the flow chart shown in FIG. 4. FIG. 5 primarily depicts the decision states which determine whether or not the channel status is closed based upon the value of the channel quality parameters. Within the state 164, the value of the error counter is read which may have been previously incremented in the state 158 (shown in FIG. 4). From this value, a relative percentage value for the error is calculated next in a state 166.

With the error percentage rate calculated, process flow enters a decision state 168 to determine whether the average noise amplitude is greater than the noise threshold value. The value of the noise threshold is predetermined and is based upon the specifications of the associated pacemaker and programmer. If the average noise amplitude is above this predetermined threshold, it is presumed that the channel status must be closed and that any meaningful data transmission has ceased. Accordingly, the process flow enters an activity state 170 which sets an appropriate flag to indicate this result. If the average noise amplitude is not greater than the threshold, the process flow will exit the decision state 168 and the communication channel will be evaluated further.

Upon exiting the decision state 168, other channel parameters which may mandate the presumption of a closed channel are evaluated in sequential decision states 172 and 174. The signal amplitude is first evaluated in the decision state 172 to determine if it is less than the signal threshold value. The value for the signal threshold is a predetermined number which is based on information related to the pacemaker and the programmer. If the signal amplitude is less than this threshold, process flow exits the decision state 172 and enters the state 170 where it is presumed that the channel status is closed. If the signal amplitude exceeds the signal threshold, process flow enters the decision state 174.

Within the decision state 174, the error rate parameter is evaluated. The error rate may be calculated as a raw number or as a percentage rate. If the error is greater than the threshold, as determined in the state 174, control then enters the state 170 indicating the channel status is closed. Assuming the response is "NO" to all three decision states 168, 172 and 174, then the process flow travels to a node 176. Likewise, after the channel status is indicated as closed within the state 170, the process flow also enters the node 176.

From the node 176, process flow enters a decision state 178 shown in FIG. 6, which figure represents the continuation of the process flow shown in FIG. 5. Within the decision state 178, the slave processor 74 determines whether the host is requesting a communication-channel status message, i.e., whether channel monitoring is requested. As will be described in more detail in conjunction with FIG. 7, the host will initially request such a message in response to a user input to monitor the channel quality. If the user selects a continuous and permanent feed of channel status information, then the slave will set a flag (in response to a state 200 shown in FIG. 7) to indicate that channel status information is to be forwarded to the host. In such a case, the answer to the question posed in the decision state 178 will always be "yes".

If the host is requesting a communication-channel status message, then the flow enters a state 180 where the data message is composed. The communication-channel status message includes an indication of the status of the channel (i.e., either open or closed), the average signal amplitude, the average noise amplitude, and the percentage of error. After the message is composed, flow enters a state 182 in which the message is sent to the host for further processing. Process flow then exits the state 182 and proceeds to the node 184. Process flow also enters the node 184 directly if it is determined that the host is not requesting a communication-channel message within the decision state 178. At node 184, flow returns to node C of FIG. 4 where the status and quality of the RF communication channel is reevaluated.

FIG. 7 depicts the process flow for the software residing in the host processor for those sequence of steps performed in monitoring the communication channel. In general, the slave processes that were previously described in conjunction with FIG. 4–6 will be simultaneously occurring with the process steps shown in FIG. 7.

As indicated in FIG. 7, the process steps undertaken in the host processor for monitoring the channel quality begin with a start state 190. From the state 190, control immediately enters an initialization state 192 similar to that of the slave processor. After the initialization state 192, control is transferred to an activity state 194 in which the "reopen" flag is reset. The status of the reopen flag will determine whether the programmer will automatically attempt to establish a communication link between the telemetry head and the stimulation device, should the communication link be lost. From the activity state 194, control enters a first decision state 196. Within the state 196, the host determines whether the user has executed some command which has generated an interface interrupt signal. If an interface interrupt is not received, control passes to a decision state 204.

Generation of an interrupt signal indicates that the user requests some operation be performed. Upon receipt of an interface interrupt within the state 196, flow enters another decision state 197. In the state 197, a determination is made whether the specific user request was a command from the user to monitor the telemetry channel. If the request was such a command, process flow enters a state 200 in which the host sends a command to the slave directing the slave to monitor the telemetry channel. In a preferred embodiment, the channel is continuously monitored in response to the associated user request. Accordingly, when the command is sent to the slave to monitor the channel during the activity of the state 200, a flag will be set by the slave indicating this request and the state 200 will not be reentered.

In an alternative embodiment, the channel quality information may only be displayed briefly in response to a selection made periodically by a user. In such a case no permanent flag will be set by the slave processor and the channel information will be forwarded to the host only upon request by the user. In such an instance, process flow will traverse the loop represented by states 196, 197 and 200 in direct response to an input from the user to monitor the channel.

If it is determined within the decision state 197 that the command was not a user request to monitor the telemetry channel, process flow enters another decision state 198. A determination is made within the state 198 whether the user is requesting that the communication channel be automatically opened. If the user is making such a request, then control enters an activity state 199 in which the automatic reopen flag is set. When the reopen flag is set, the programmer will automatically reopen the communication channel whenever it closes, i.e., whenever state 170 of FIG. 5 is entered. After the reopen flag is set in the state 199, control passes to the decision state 204.

If the user is not requesting activation of the automatic reopen feature, as determined in the state 198, control passes to an activity state 202. The state 202 represents the processing activities required for user requests other than the channel-monitoring request, or the automatic reopen request. The state 202 will thus be entered from the decision state 198 once a permanent flag is set in the state 200, and if the user does not request automatic reopening of the communication channel. Process flow then proceeds to the decision state 204 as discussed below.

If no user interrupt was received in the state 196, or after flow has exited the states 199, 200, and 202, the system enters the decision state 204. In this state, the host determines whether an interface interrupt signal was received from the slave processor. If such an interrupt was received, flow exits the decision state 204 and enters a state 206. If no interrupt was received from the slave, control reverts back to the state 196. The interrupt received in the decision state 204 indicates that a message was transferred from the slave. This message is processed in the state 206 and flow subsequently enters another decision state 208. Within this decision state, the host determines whether the slave message is a message indicating the status and quality of the telemetry channel. If the slave message was not a channel quality message, process flow enters an activity state 209 in which the required operation for addressing the message is performed by the host processor 72. The state 209 represents processing, other than that for monitoring the communication channel quality, which is performed by the host processor 72 during a typical procedure for programming and/or monitoring the function of a pacemaker. After the appropriate operations are performed in the state 209, control also reverts back to the decision state 196.

Assuming a channel quality status message was transmitted by the slave, process flow exits the decision state 208 and enters a state 210. Within the state 210, the signal-to-noise ratio is calculated by the host processor and the value of the average signal amplitude is normalized within a predetermined scale. For example, the value of the signal amplitude will be normalized within the range of zero, indicating the presence of no signal, to one, indicating the highest possible signal amplitude. From the state 210 flow enters a state 212 which represents the processing required to update the communication channel information, and visually display the parameters representing channel status and quality. Such visual displays may include a channel status icon, a signal amplitude display, a signal-to-noise ratio display, and a percentage error rate display. These visual displays will be described below in conjunction with FIGS. 9–13. After updating the communication channel information, flow exits the state 212 and enters a decision state 214. Within the decision state 214, two determinations are made. The first is whether the automatic reopen flag has been enabled, i.e., whether the reopen flag was set in the state 199. The second determination is whether the channel status, as updated in the state 212, is now closed. If the answer to these determinations is positive, flow enters an activity state 216 in which an open-channel message request is composed. Process flow then directly enters the activity state 202. The open-channel message will cause the slave processor flow to enter the state 147 (shown in FIG. 4) and reopen the communication channel. If the answer to either of the determinations made in the state 214 is negative, flow merely reverts back to the state 196.

As described in conjunction with FIGS. 4–7 above, the interaction between portions of the software architecture 81 (shown in FIG. 3) residing in the host processor and the slave processor allow for the continuous monitoring of the telemetry channel. This monitoring and corresponding display of the information is performed simultaneously with other programming and monitoring procedures performed by the programmer 30 (shown in FIG. 1).

Figure 8:
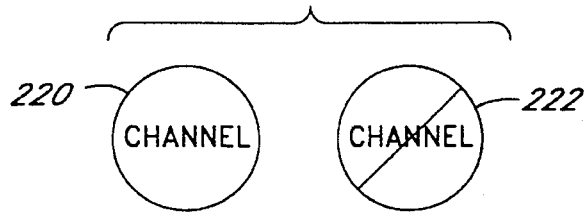
FIG. 8 is a graphical representation of indicia depicting the communication channel status in accordance with the present invention.

FIGS. 8–12 depict the preferred visual displays for conveying channel status and quality information to an operator of the programmer 30 (shown in FIG. 1). The first graphical display, or icon, which can be conveyed to an operator is the status of the channel itself. As described before, the channel can have only two states, either open or closed. Accordingly, this graphical icon has two display states 220, 222, both of which are represented in FIG. 8. When the display 220 is presented to the user, this indicates that the communication channel is open and data may be transmitted between the pacemaker 52 and the programmer 30 (shown in FIG. 1). Conversely, when the display 222 is presented to the user, this indicates that the communication channel is closed.

Figure 9:
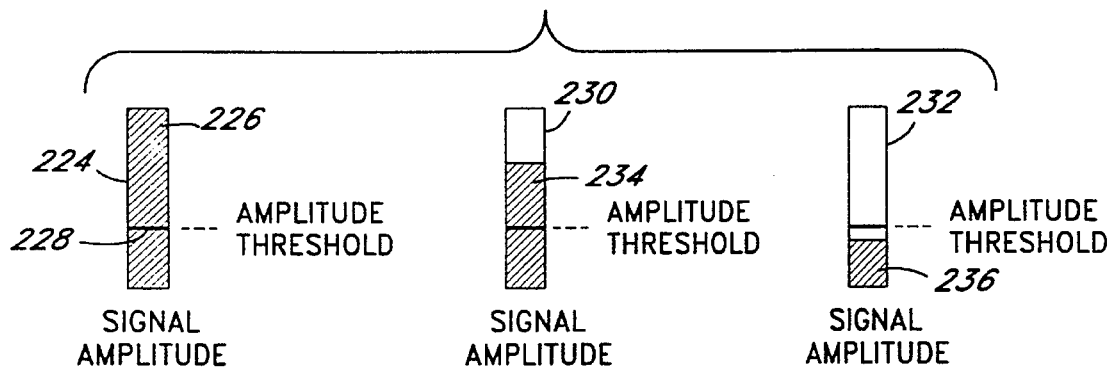
FIG. 9 is a graphical representation of indicia depicting the signal amplitude in accordance with the present invention.

FIG. 9 illustrates three separate graphical representations for conveying information regarding the signal amplitude. The displays for this parameter will preferably consist of a bar graph 224 having a shaded portion 226 indicating the relative value of the signal amplitude. A marker 228 is graphically displayed as part of the bar graph 224 to indicate a threshold of signal amplitude which must be maintained. This threshold value corresponds to the threshold value described with respect to the decision state 172 of FIG. 5. Two other possible values for the signal amplitude are shown in connection with a bar graph 230 and a bar graph 232. These bar graphs 230 and 232 have corresponding shaded portions 234 and 236 which represent various levels of signal amplitude.

Figure 10:
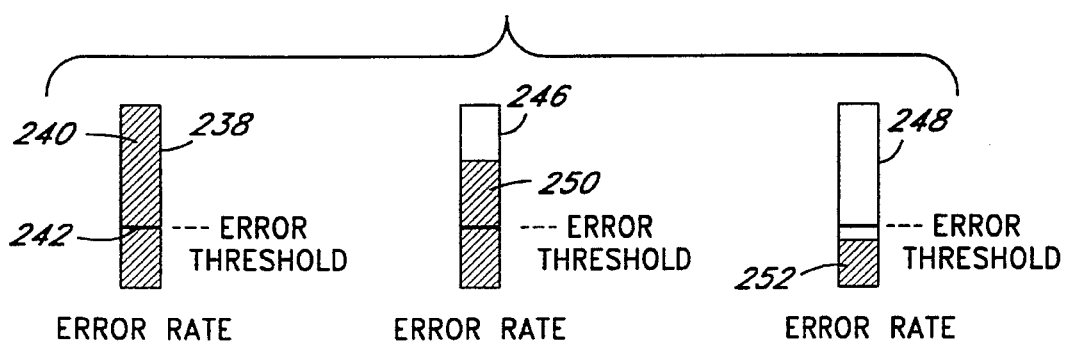
FIG. 10 is a graphical representation of indicia depicting the error rate in accordance with the present invention.

FIG. 10 illustrates three separate graphical representations of the error rate associated with data transmission over the RF communication channel 62 (shown in FIG. 1). A first bar graph 238 is shown having a shaded portion 240 which represents the error rate resulting from data transmission. A marker 242 is used as part of the graphical representation to indicate a demarcation between acceptable and unacceptable error threshold levels. If the error rate goes above the marker 242, the data transmitted over the RF communication channel will not be accurate and the communication channel will be considered closed. Such a decision corresponds with that made in the decision block 174 shown in FIG. 5. The remaining two graphical representations depict varying levels of error occurring during data transmission. Specifically, a bar graph 246 is shown with an error rate indicated by the shaded region 250 which is above the error threshold. A separate bar graph 248 is shown in which the value of the error rate depicted by shaded region 252 is below the error threshold.

Although three possible values for the signal level parameter and the error rate parameter are depicted as separate bar graphs in FIGS. 9 and 10, this is for illustrative purposes only. In operation, the screen segment 70, or the video display screen 35 (shown in FIG. 1), of the programmer 30 (shown in FIG. 1) will display only one bar graph for the channel parameter shown in FIG. 9, and one bar graph for the channel parameter shown in FIG. 10.

Although only the signal level and error rate are depicted in FIGS. 9 and 10, it can be appreciated that other channel quality parameters can be depicted in the same manner. For example, a separate bar graph representing the noise amplitude level can also be displayed on the screen segment 70, or the segment 35.

FIG. 11 is an illustration of a parameter indicative of the noise level. As shown, a signal-to-noise ratio may be displayed as a number 256 which has been calculated by the host processor 72 (shown in FIG. 2). The number 256 represents the average signal-to-noise ratio resulting from communication with a pacemaker over a given interval. The number 256 is calculated in the state 210 (shown in FIG. 7) based on the measurements made in the state 154 (shown in FIG. 4). The signal-to-noise ratio 256 illustrated in FIG. 11 may be continuously displayed, or such information, and other channel related information, may be selectively displayed by the user.

Visual information representing the communication channel status and quality may be presented in a number of different formats. Each format may be unique and provide its own advantages in determining the status and quality of the communication channel. Distinct formats may be chosen depending on the desired medical procedure, use of a certain programmer, or use of a certain pacemaker.

FIG. 12 is an illustration of a video display screen 35 which is used for monitoring and/or programming a pacemaker. The video display screen 35 is in a format typical of that seen during a monitoring session for a cardiac pacemaker. Specifically, waveforms 260 and 262 represent the cardiac functions of a patient's heart which are displayed in real-time. During this real-time procedure, graphical representations of the channel status and quality are continuously displayed and updated within the display segment 70. These channel parameters include a channel status icon 266, a signal strength meter 268, an error rate meter 270, and a representation 272 of the signal-to-noise ratio. Channel parameters 266, 268, 270, and 272 may be displayed in the screen segment 38 depending upon the particular monitoring procedure, or depending on the preferences of a user. Moreover, the channel parameters 266, 268, 270, and 272 may be displayed on a separate display screen which is part of the telemetry head itself (not shown). For a complete description of a telemetry wand having a display and controls for a medical device, see the U.S. Pat. Nos. 5,311,449 and 5,336,245, which are hereby incorporated herein by reference.

As can be seen in conjunction with FIG. 12, when an attending physician is viewing the video screen 35 during a monitoring procedure, the physician receives instant feedback of the channel status and quality from the segment 70. This instant feedback allows an attending physician to quickly discover that the communication channel is either already closed, or that the channel is fading. Instant channel feedback can be especially important where symbols, instead of a dynamic waveform, are displayed on the segment 38 to represent the monitored cardiac events. With such feedback, the physician is not only alerted that a problem with the communication channel exists, but by viewing which aspect of the channel quality is fading, the physician is also directed to the source of the problem. For example, a low reading on the signal level meter 268 indicates that the telemetry head (not shown) needs to be closer to the cardiac stimulation device (not shown). A low signal-to-noise ratio indicates proximity to high-noise equipment, indicating that the patient or the high-noise equipment needs to be isolated. It can be appreciated that various different graphical representations may be used to convey the same type of channel quality information displayed in the segment 70 of the video screen 35.

Through the foregoing description and accompanying drawings, the present invention has been shown to have important advantages over current devices and methods used to communicate with and program a cardiac stimulation device. While the above detailed description has shown, described, and pointed out the fundamental novel features of the invention, it will be understood that various omissions and substitutions and changes in the form and details of the device and process illustrated may be made by those skilled in the art, without departing from the spirit of the invention. Therefore, the invention should be limited in its scope only by the following claims.

What is claimed is:

1. An external monitoring apparatus having a communication channel for transmitting signals representing data between a cardiac stimulation device implanted within a human body and the external monitoring apparatus, comprising:

a telemetry head, connected to the external monitoring apparatus, having means for transmitting and receiving radio frequency signals, defined by a plurality of parameters, over the communication channel;

means for measuring at least one parameter of the radio frequency signals, the measured parameter being indicative of the quality of the communication channel;

means for evaluating the quality of the communication channel based on the value of the measured parameter; and means for displaying at least one graphical representation indicative of the quality to an operator.

2. The apparatus of claim 1, wherein:

the measuring means includes means for repeatedly measuring the parameter during transmission and reception of the radio frequency signals.

3. The apparatus of claim 1, wherein:

the measured parameter is a parameter that indicates signal level of the radio frequency signals.

4. The apparatus of claim 1, wherein:

the measured parameter is a parameter that indicates noise level.

5. The apparatus of claim 1, wherein:

the measured parameter is a parameter that indicates error transmission rate of the data.

6. The apparatus of claim 1, wherein:

the measured parameter is a single parameter that indicates signal-to-noise ratio of the radio frequency signals.

7. The apparatus of claim 1, wherein:

the measuring means includes means for measuring at least first and second parameters, the first parameter indicative of the level of the signal representing the data and the second parameter indicative of an error transmission rate of the data.

8. The apparatus of claim 1, wherein:

the measuring means includes means for measuring at least first and second parameters, the first parameter indicative of the level of the signal representing the data and the second parameter indicative of the level of noise received by the telemetry head.

9. The apparatus of claim 1, further comprising:

means for determining whether the operative status of the communication channel is open or closed based on the value of the measured parameter.

10. The apparatus of claim 9, wherein:

the measured parameter is a single parameter that indicates the level of the signal representing the radio frequency data; and the verifying means includes means for providing a signal indicating that the communication channel is closed when the measured parameter is less than a first predetermined level.

11. The apparatus of claim 9, wherein:

the measuring means includes means for measuring at least first and second parameters, the measured first parameter indicative of the level of the signal representing the data and the second parameter indicative of the level of noise received by the telemetry head; and the verifying means includes means for providing a signal indicating that the communication channel is closed when the first parameter is less than a first predetermined level, and provides a signal indicating that the channel is closed when the second parameter exceeds a second predetermined level.

12. The apparatus of claim 1, wherein the displaying means comprises:

means for conveying the information to the operator on at least one of the telemetry head or the external monitoring apparatus.

13. An external monitoring apparatus, having a telemetry device coupled to a control unit, for monitoring the status and quality of a radio frequency communication channel used to transmit and receive signals defined by a plurality of parameters, including data signals, between a cardiac stimulation device implanted within a patient and said telemetry device, said apparatus comprising:

means for establishing said communication channel by initiating a coded data transmission between said cardiac stimulation device and said control unit;

means for dynamically measuring at least one parameter of the signals transmitted over the channel, the dynamic measuring means comprising means for dynamically measuring a first parameter indicative of the communication channel quality during transmission of the data signals;

means, coupled to the dynamic measuring means, for determining the operative status of said communication channel;

means for generating a data message indicative of the communication channel status and quality; and means, responsive to the data message, for displaying a representation of the communication channel status and quality, said displaying means comprising means for displaying a graphical representation of the first parameter to provide feedback information to an operator of said control unit for positioning of said telemetry device in response to the feedback information.

14. The apparatus of claim 13, wherein:

the first parameter is an amplitude level of the signal transmitted from the cardiac stimulation device.

15. The apparatus of claim 13, wherein:

the first parameter is a noise level of the signal transmitted from the cardiac stimulation device.

16. The apparatus of claim 13, wherein:

the first parameter is a signal-to-noise ratio of the signal transmitted from the cardiac stimulation device.

17. The apparatus of claim 13, wherein:

the first parameter is an error rate of the signal transmitted from the cardiac stimulation device.

18. The apparatus of claim 13, wherein said dynamic measuring means further comprises:

means for dynamically measuring a second parameter indicative of said communication channel quality during transmission of the data signals to provide additional feedback information to the operator of said control unit for improving the communication channel between said cardiac stimulation device and said telemetry device.

19. The apparatus of claim 18, wherein:

the displaying means comprises means for displaying a graphical representation of the second parameter.

20. The apparatus of claim 13, wherein the means for determining the operative status comprises:

means for determining the level of the first parameter; and means for determining the operative status based upon the level of the first parameter.

21. The apparatus of claim 13, wherein:

the displaying means comprises a video display screen attached to the control unit so that an operator of the control unit can receive feedback information for improving the communication channel between the cardiac stimulation device and the telemetry device.

22. The apparatus of claim 13, wherein:

the displaying means comprises a display screen attached to the telemetry device so that an operator of the telemetry device can receive feedback information for improving the communication channel between the cardiac stimulation device and the telemetry device.

23. The apparatus of claim 13, wherein:

the first parameter is a signal-to-noise ratio and the second parameter is a data-transmission error rate.

24. The apparatus of claim 13, wherein:

the first parameter is the signal level emanating from the cardiac stimulation device.

25. The apparatus of claim 13, wherein the measuring means further comprises:

means for averaging successive measured values of said first parameter over a predetermined interval during the transmission of the data signals.

26. A programming device having an apparatus for evaluating a radio frequency communication channel between a cardiac stimulation device implanted within a patient and the programming device, comprising:

a telemetry head, connected to said programming device, having means for transmitting radio frequency signals to said cardiac stimulation device and for receiving radio frequency signals from said cardiac stimulation device, said radio frequency signals being defined by a plurality of parameters and representing data exchanged between said cardiac stimulation device and said programming device during a procedure for programming or monitoring said cardiac stimulation device;

means for establishing said radio frequency communication channel between said cardiac stimulation device and said telemetry head;

means for displaying said data to an operator of said programming device during said procedure;

means for measuring a first parameter during said procedure, said first parameter indicative of the strength of said radio frequency signals emanating from said cardiac stimulation device;

means for measuring a second parameter during said procedure, said second parameter indicative of the strength of signals emanating from sources other than said cardiac stimulation device; and means for displaying a graphical representation of said first and second parameters to said operator during said procedure.

27. The apparatus of claim 26, further comprising:

means for determining when said first parameter has a value less than a first predetermined value and for determining when said second parameter has a value which exceeds a second predetermined value; and means for providing a signal indicating that the communication channel is closed when at least one of said first parameter is less than said first predetermined level or said second parameter has a value which exceeds said second predetermined value.

28. The apparatus of claim 26, further comprising:

means for determining when said first parameter has a value less than a first predetermined value; and means, coupled to the means for displaying, for generating an icon having a first state and a second state, wherein said first state is displayed when said first parameter is greater than or equal to said first predetermined value corresponding to the communication channel being open, and said second state is displayed when said first parameter is less than said first predetermined value corresponding to the communication channel being closed.

29. The apparatus of claim 26, further comprising:

means for determining when said second parameter has a value which exceeds a second determined value; and means, coupled to the means for displaying, for generating an icon having a first state and a second state, wherein said first state is displayed when said second parameter has a value which is less than or equal to said second predetermined value corresponding to the communication channel being open, and said second state is displayed when said second parameter exceeds said second predetermined value.

30. The apparatus of claim 26, further comprising:

means for detecting a number of incorrect bits in said data transmitted through the radio frequency communication channel during a predetermined time interval and for determining an error rate thereof; and means for displaying a graphical representation of said error rate to said operator during said procedure.

31. The apparatus of claim 30, further comprising:

means for determining when said error rate has a value which exceeds a third predetermined value; and means coupled to the means for displaying, for generating an icon having a first state and a second state, wherein said first state is displayed when said error rate has a value which is less than or equal to the third predetermined value corresponding to the communication channel being open, and said second state is displayed when said error rate exceeds the third predetermined value corresponding to the communication channel being closed.

32. The apparatus of claim 26, wherein the measuring means further comprises:

means for averaging said first parameter over a predetermined length of time to produce an average strength of said radio frequency signals emanating from said cardiac stimulation device; and means for averaging said second parameter over a predetermined length of time to produce an average strength of signals emanating from sources other than said cardiac stimulation device.

33. The apparatus of claim 26, further comprising:

means for determining a ratio of said first and second parameters; and wherein said means for displaying said graphical representation of said first and second parameters comprises means for generating an icon indicating the ratio of said first parameter to said second parameter.

34. The apparatus of claim 26, wherein:

said means for measuring said first parameter and said means for measuring said second parameter include means for operating continuously with said transmission and reception of said radio frequency signals.

35. An external monitoring device having an apparatus for providing information about a communication channel over which data is transmitted between a cardiac stimulation device implanted within a human body and said external monitoring device, comprising:

a telemetry head, connected to said external monitoring device, having means for transmitting and receiving radio frequency signals, defined by a set of parameters, over said communication channel, said signals representative of said data, said data reflective of functions performed by the cardiac stimulation device;

means for processing said data within said external monitoring device;

a display for conveying said data to an operator of said external monitoring device;

means for monitoring at least one parameter within the set of parameters, each parameter in the set indicative of a quality aspect of the communication channel, the set of parameters comprising:

(a) a first parameter indicating the strength of said radio frequency signals emanating from said cardiac stimulation device;

(b) a second parameter indicating the strength of signals emanating from sources other than said cardiac stimulation device;

(c) a third parameter indicating an error rate associated with transmission of said data between said cardiac stimulation device and said programming unit; and means for generating icons representing at least one of the parameters, the generating means including means for displaying said icons onto said display to provide feedback of communication-channel information to said operator.

36. The apparatus described in claim 35, further comprising:

means for processing at least one of the set of parameters to determine whether said communication channel is open or closed, the processing means including:

means for measuring an amplitude of at least one of the set of parameters; and means for determining when said amplitude meets a prescribed criteria which defines an open and a closed communication channel.

37. The apparatus described in claim 35, wherein:
said means for monitoring comprises means for averaging said parameters over a predetermined period of time before being displayed to said operator.

38. The apparatus described in claim 35, wherein:
said means for monitoring said second parameter comprises means for determining the ratio of a signal level to a noise level.

39. The apparatus described in claim 35, wherein:
said graphical icons comprise a signal meter corresponding to the magnitude of said signals and an error-rate meter corresponding to the magnitude of the error rate associated with transmission of said data.

40. The apparatus described in claim 35, wherein:
said graphical icons comprise a signal meter corresponding to the magnitude of said signals and a signal-to-noise ratio indicator.

41. A method of continuously monitoring and displaying operational information of a telemetry link, said telemetry link transmitting data between a cardiac stimulation device and a processing unit having a telemetry head and a display screen, said method comprising the steps of:
(1) establishing a telemetry link between said cardiac stimulation device and said telemetry head for the transmission and reception of telemetry signals;
(2) generating a request signal by said processing unit to initiate monitoring of the telemetry link;
(3) determining at least one parameter corresponding to the quality of a telemetry signal received by said telemetry head;
(4) verifying the status of said telemetry link between said pacemaker device and said telemetry head, the status being one of open or closed;
(5) generating a channel-information data message based on the results of steps (3) and (4) for indicating the status of the telemetry link and the quality of said telemetry signal;
(6) processing said channel-information data message for display; and
(7) displaying said channel-information data message as at least one dynamically-changing icon on the display screen.

42. The method, as recited in claim 41, wherein the step (7) of displaying said channel-information message comprises the steps of:
displaying first and second icons, said first icon having an "open" or a "closed" status symbol corresponding to the status of said telemetry link as verified in step (4), and said second icon having a "quality" symbol for conveying the quality of the signal as determined in step (3); and
wherein the processing step (6) comprises updating said first and second icons in real-time by generating subsequent channel-information data messages and processing said data messages for display.

43. The method, as recited in claim 42, wherein the step (3) of determining a parameter corresponding to the quality of a telemetry signal further comprises the steps of:
determining signal strength of the telemetry signal; and
defining signal strength as a first parameter corresponding to the quality of a telemetry signal received by said telemetry head.

44. The method, as recited in claim 43, wherein the step of determining signal further comprises the steps of:
determining a noise signal of the telemetry signal by measuring the signal strength of all signals received by said telemetry head when said cardiac stimulation device is not transmitting telemetry signals; and
comparing the level of the noise signal with the level of the telemetry signal to produce a signal-to-noise ratio; and
defining the signal-to-noise ratio as a second parameter corresponding to the quality of a telemetry signal received by said telemetry head.

45. The method, as recited in claim 44, further comprising the steps of:
processing the noise signal for display; and
displaying a third icon comprising a symbol for indicating the relative value of the noise signal.

46. The method, as recited in claim 41, further comprising the steps of:
determining an error rate by detecting the number of incorrect data signals received by said processing unit over a described time interval; and
displaying a representation of said error rate.

47. The method, as recited in claim 41, wherein the step of displaying (7) comprises the step of:
displaying said dynamically-changing icons on a display screen of said processing unit.

48. The method, as recited in claim 41, wherein the step of displaying (7) comprises the step of:
displaying said dynamically-changing icons on a display screen located on said telemetry head.

49. An external monitoring device having an improved communication system for transmitting and receiving telemetry signals between an implantable cardiac stimulation device and the external monitoring system, the improved communication system comprising:
a telemetry head having means for transmitting and receiving the telemetry signals, the telemetry signals being defined by a plurality of parameters;
means for measuring at least two parameters of the telemetry signals indicative of the quality of the telemetry signals received from the implantable device; and
display means for displaying the at least two parameters indicative of the quality of the telemetry signal so that appropriate action can be taken by an operator to establish and maintain a proper communication link.

50. The system of claim 49, wherein a first parameter of the at least two parameters indicative of the quality of the communication channel is signal amplitude.

51. The system of claim 50, further comprising means for graphically displaying the first parameter on the display means.

52. The system of claim 50, wherein a second parameter of the at least two parameters indicative of the quality of the communication channel is one of noise amplitude, error transmission rate, or signal-to noise ratio.

53. The system of claim 52, further comprising means for graphically displaying the second parameter on the display means.

54. The system of claim 49, wherein:
the measuring means includes means for repeatedly measuring the at least two parameters during transmission and reception of the telemetry signals; and
the display means includes means for dynamically updating the at least two parameters indicative of the quality of the signal.

55. The system of claim 49, further comprising:

means, coupled to the measuring means, for determining whether the operative status of the communication channel is either open or closed based on the values of the at least two parameters; and means for displaying the operative status on at least one of the telemetry head or the external monitoring device.

56. The system of claim 55, further comprising:

means for confirming the status of the communication channel by verifying the exchange of data between the cardiac stimulation device and the external monitoring device.

57. The system of claim 49, further comprising:

processing means for determining whether the communication channel is open or closed, the processing means including:

means for measuring an amplitude of the at least two parameters;

means for determining when the amplitudes meet a prescribed criteria which defines an open and a closed communication channel; and means for displaying the operative status on at least one of the telemetry head or the external monitoring device.

58. An external monitoring device having an improved communication system for transmitting and receiving telemetry signals carrying data between an implantable cardiac stimulation device and the external monitoring system, the improved communication system comprising:

telemetry means for transmitting and receiving the telemetry signals;

means for determining an error rate of the telemetry signals, the error rate being defined as a number of incorrect bits in the data transmitted by the telemetry signal during a predetermined time interval; and means for displaying the error rate to an operator of the programming device.

59. The apparatus of claim 58, further comprising:

means for measuring a signal strength of the telemetry signals; and means for displaying the signal strength to an operator of the programming device.

60. The apparatus of claim 58, further comprising:

means for measuring a noise signal strength of the telemetry signals; and means for displaying the noise signal strength to an operator of the programming device.

61. The apparatus of claim 58, further comprising:

means for measuring a signal strength of the telemetry signals;

means for measuring a noise signal strength of the telemetry signals; and means for displaying the signal-to-noise strength to an operator of the programming device.

62. The apparatus of claim 61, further comprising:

means, coupled to the measuring means, for determining whether the operative status of the communication channel is open or closed based on the values of the at least two channel quality indicators selected from the group of the error rate, the signal strength, the noise signal strength, and the signal-to-noise ratio; and means for displaying the operative status on at least one of the telemetry head or the external monitoring device.

* * * * *